(12) United States Patent
Haines

(10) Patent No.: US 10,429,355 B2
(45) Date of Patent: Oct. 1, 2019

(54) MINIMUM REDUNDANCY SPACING FUNCTIONS FOR SURFACE ACOUSTIC WAVE (SAW) SENSOR DEVICES

(71) Applicant: Mnemonics, Inc., Melbourne, FL (US)

(72) Inventor: D. Mark Haines, Melbourne, FL (US)

(73) Assignee: MNEMONICS, INC., Melbourne, FL (US)

( * ) Notice: Subject to any disclaimer, the term of this patent is extended or adjusted under 35 U.S.C. 154(b) by 304 days.

(21) Appl. No.: 15/268,307

(22) Filed: Sep. 16, 2016

(65) Prior Publication Data

US 2017/0074835 A1 Mar. 16, 2017

Related U.S. Application Data

(60) Provisional application No. 62/219,230, filed on Sep. 16, 2015.

(51) Int. Cl.
*G01N 29/24* (2006.01)
*H03H 9/02* (2006.01)
(Continued)

(52) U.S. Cl.
CPC ....... *G01N 29/2462* (2013.01); *G01K 11/265* (2013.01); *G01L 1/255* (2013.01); *H03H 9/02637* (2013.01); *G01N 2291/011* (2013.01); *G01N 2291/02827* (2013.01); *G01N 2291/02872* (2013.01); *G01N 2291/02881* (2013.01); *G01N 2291/045* (2013.01)

(58) Field of Classification Search
CPC ......... G01N 29/2462; G01N 2291/011; G01K 11/265; G01L 1/255; H03H 9/02637
See application file for complete search history.

(56) References Cited

U.S. PATENT DOCUMENTS

| | | | | | |
|---|---|---|---|---|---|
| 5,821,425 | A | * | 10/1998 | Mariani | G01N 29/022 73/703 |
| 2002/0005677 | A1 | * | 1/2002 | Reindl | H03H 9/6406 310/313 D |

(Continued)

OTHER PUBLICATIONS

Alan T Moffet, Minimum-Redundancy Linear Arrays, IEE Transaction on Antennas and Propagation, vol. AP-16, No. 2, Mar. 1968.*
(Continued)

*Primary Examiner* — Mohamed Charioui
*Assistant Examiner* — Catherine T. Rastovski
(74) *Attorney, Agent, or Firm* — Beusse, Wolter, Sanks & Maire PLLC; John L. DeAngelis

(57) ABSTRACT

A surface acoustic wave sensor system for determining environmental conditions on a substrate. The system comprises an interrogator for producing an RF interrogating signal transmitted by an antenna to an interdigital transducer mounted on the substrate for producing an incident surface acoustic wave responsive to the interrogating signal. A plurality of reflector arrays mounted on the substrate produce a like plurality of reflected surface acoustic waves; a spacing between adjacent ones of the plurality of reflector arrays comprising a non-uniform distance. The plurality of reflected surface acoustic waves are responsive to the environmental condition and exhibit a characteristic from which the environmental condition can be determined by a processing component.

18 Claims, 11 Drawing Sheets

(51) Int. Cl.
*G01L 1/25* (2006.01)
*G01K 11/26* (2006.01)

(56) References Cited

U.S. PATENT DOCUMENTS

| | | | | |
|---|---|---|---|---|
| 2013/0036821 A1* | 2/2013 | Belkerdid | ............ | G01N 29/041 73/627 |
| 2015/0013461 A1* | 1/2015 | Pollard | ............... | H01L 41/1132 73/579 |
| 2016/0258908 A1* | 9/2016 | Goto | ................. | G01N 29/2462 |

OTHER PUBLICATIONS

Belknap, E. "Mechanical Characterization of SAW-Based Sensors for Wireless High Temperature Strain Measurements." 2011, The Ohio State University, Mechanical Engineering Graduate Program thesis.
Moffet, A.T. "Minimum-Redundancy Linear Arrays," IEEE Trans. Antenn. Propag. 16(2), 172-175 (1968).
Helfer, T.T., Welch, W.J. "Minimum Redundancy Linear Arrays," BIMA Memo 54, 1-4 (1997).
Chen, C.Y., Vaidyanathan P. P. "Minimum Redundancy Mimo Radars," IEEE Intern. Symp. on Circuits & Systems, Seattle, WA, 45-48 (2008).

* cited by examiner

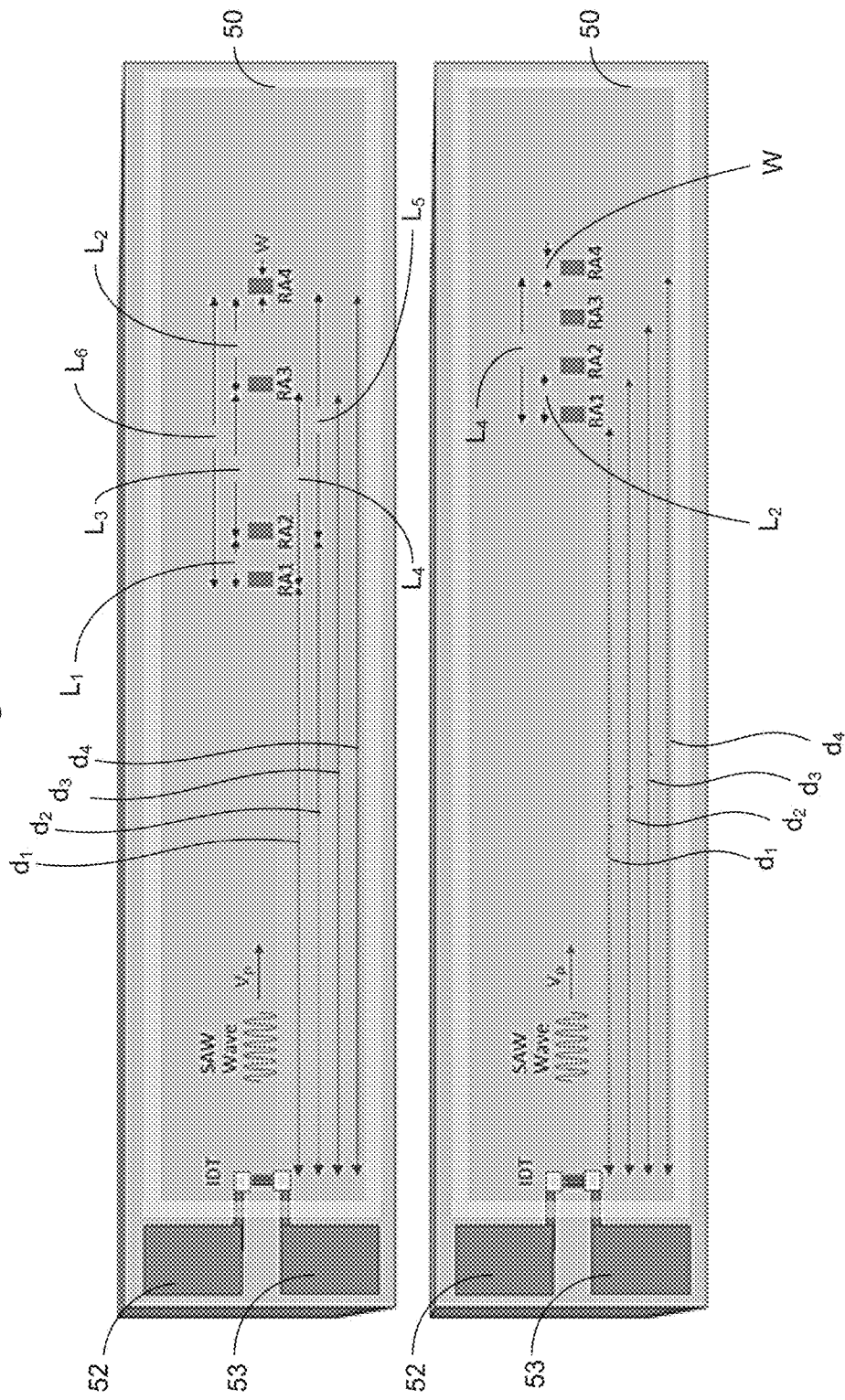

MINIMUM REDUNDANCY SPACING FUNCTIONS FOR SURFACE ACOUSTIC WAVE (SAW) SENSOR DEVICES

CROSS REFERENCE TO RELATED APPLICATIONS

The present application claim priority under Section 119(e) to the provisional application filed on Sep. 16, 2015, assigned application No. 62/219,230 and entitled Minimum Redundancy Spacing Functions for Surface Acoustic Wave (SAW) Sensor Devices, which is incorporated herein in its entirety.

FIELD OF THE INVENTION

The present invention relates generally to surface acoustic wave (SAW) device sensors and in particular to SAW device with a specified distance between individual reflector arrays as mounted on the SAW substrate to provide an accurate measurement of physical dimensional changes in the substrate.

BACKGROUND OF THE INVENTION

Passive-Wireless SAW (PWSAW) sensors have been produced for remote sensing of temperature and strain, and by using specially designed packages, the strain sensors have been adapted for use as torque or pressure sensors. Also the PWSAW devices have been used as short range radar transponders that facilitate the measurement of distance, speed and revolutions per minute (RPM).

The PWSAW sensor devices use the properties of a piezoelectric substrate material to convert a received RF interrogation pulse into an acoustic wave that travels on the surface of the substrate; thus, the name Surface Acoustic Wave (SAW). As shown in FIG. 1, a PWSAW device 8 comprises a Radio Frequency (RF) transceiver 10 for generating an interrogation pulse 12 that is transmitted from an antenna 14 through the air and received by an antenna 16 attached to the PWSAW device 8.

The received RF signal is then applied to an Interdigital Transducer (IDT) 22 consisting of metal electrodes or "fingers" 26 etched on the surface 28A of the piezoelectric substrate 28.

The IDT 22 generates a SAW pulse 30 that propagates to a series of reflector arrays (RAs) 32, which each RA also comprising a plurality of metal electrodes or "fingers" 34. Each finger 34 in an RA reflects a small portion of the remaining energy in the incident SAW wave. However, these "sub-echoes" from each finger are designed to be coherent with each other, so their sum can be treated as a single echo from the RA (the sum echo referred to herein as a reflected SAW or echo).

When these RA echoes reach the IDT 22, they are converted back to electrical signals (an electrical echo pulse) and immediately radiate from the attached antenna 16 back to the transceiver 10 where they are processed to produce sensor data.

The transceiver 10 is controlled to operate in a transmitting mode to transmit the interrogation pulse 12 during a first interval and later in a receiving mode to receive the electrical echo pulse during a second interval.

FIG. 2 illustrates propagating SAWs 44 on the substrate 28.

Stress in the crystalline structure of the piezoelectric substrate changes when its temperature changes or when mechanical forces are applied to it. This stress changes the propagation velocity ($V_p$) of the SAW wave from the value of the propagation velocity in the absence of any imposed stresses. With a change in the propagation velocity the differential time delay and the differential phase shift are similarly changed. Here time delay refers to the time difference between receipt of an echo from a first RA and an echo from an adjacent second RA. Similarly, the phase shift refers to the phase shift between these echoes received from the first and second RAs.

The round-trip propagation time for a SAW from a time when it is launched from the IDT, reflected from the $i^{th}$ RA, and returned to the IDT is determined by $V_p$ and by the distance to the $i^{th}$ RA ($d_i$). This round-trip propagation time is given by:

$$\tau_i = (2 * d_i)/V_p \quad [1a]$$

The value $\tau_i$ may also be referred to herein as a delay time representing a time interval between launching of an incident SAW from the IDT and returning of the echo or reflected SAW from the $i^{th}$ RA back to the IDT.

For all cases of practical interest the distance traveled by the SAW signal on the substrate is two-way; therefore, it is useful to define a two-way propagation velocity, $V_{p2}$, to avoid the need to double distances when performing calculations. By dividing the numerator and denominator in Equation [1a] by a factor of two, we get $$\tau_i = d_i/V_{p2} \quad [1b]$$

where $V_{p2}$ is half the value of $V_p$.

For a Y-cut lithium-niobate substrate at 25° C., $V_p$ is 3488 m/sec, and $V_{p2}$ is 1744 m/sec or 1.744 µm/nsec, as expressed in units that are more useful for design analysis.

Since both the RF signal and the resulting SAW are sinusoidal waves, the absolute phases of the RA echoes ($\phi_i$) are determined by the absolute time delays of the RA echoes ($\tau_i$) as set forth in Equations [3a] and [3b] below.

The delay $\tau_i$ will be many times or multiples of the period (P) of the sinusoidal carrier signal plus some fraction ($\Delta P$).

Note that P is $1/f_c$, where $f_c$ is the carrier frequency (e.g., $f_c=430$ MHz or $f_c=900$ MHz) of both the RF or SAW wave.

The echo signal received at the RF transceiver exhibits a phase consistent with this fractional part, $\Delta P$, and because each cycle of a sine wave is indistinguishable from previous or later cycles, the integer periods of P are ambiguous and can be removed by using a modulo function.

But the remaining fractional part, $\Delta P$, is very significant and in fact forms the basis of the sensor measurements.

The phase of the echo signal is given by $$\phi_i = 2\pi\tau_i/P \text{ or } \phi_i = 2\pi f_c \tau_i \quad [2]$$

noting that $\tau_i$ is actually "$\tau_i$ modulo P", which removes ambiguous integer multiples of P.

From Equation [1b] above, and considering thermal effects on the distance-related parameters, the propagation velocity is more accurately given as a function of the temperature T according to the equation $$\tau_i(T) = (d_i/V_{P2})*(1+((T-25)*TCD)) \quad [3a]$$

where $d_i$, $V_{P2}$, and $V_P$ are only defined at T=25° C., which therefore requires the use of the thermal coefficient of delay parameter (TCD) in the above equation for other values of "T".

And substituting equation [3a] into equation [2]

$$\phi_i(T) = 2\pi f_c \tau_i(T) = 2\pi f_c (d_i/V_{P2})*(1+((T-25)*TCD)) \quad [3b]$$

Equation [3b] illustrates the role of $V_{p2}$ and $d_i$ in determining the echo phase.

Recall that the effect of temperature or strain on the substrate is to change $V_p$, which according to equation [1a], inversely changes the time delay ($\tau_i$). The change in delay is nearly linear with temperature and is called the Thermal Coefficient of Delay (TCD), which is well documented for the various materials used in SAW fabrication and appears in Equations [3a] and [3b] above. For instance, for lithium-niobate the TCD is 94 parts-per-million/° C. (94 ppm/° C.). By noting that $d_i$ and $V_{p2}$ are only defined at 25° C. we can now see how the sensor works by making $\tau_i$ and $\phi_i$ dependent on the temperature (T) of the substrate.

Note that the distances $d_i$ or differential distances ($d_j-d_i$), are actual physical distances when measured at 25° C., therefore Equations [1a], [1b], [3a], and [3b] are correct for $V_P$ or $V_{P2}$ which are also defined only at 25° C. But, while $V_P$, $\tau_i$ and $\phi_i$ change proportionately with temperature according to the coefficient, TCD, the distances, $d_i$ or ($d_i-d_j$), do not change proportionately. TCD therefore represents a combined effect, partly caused by a change in physical distance (i.e., expansion or contraction) and partly by a change in the stiffness of the crystalline substrate. TCD is several times larger than the coefficient of thermal expansion (CTE). Since it is not strictly correct to scale the separation distances by TCD, in this document all references to "$d_i$" should be interpreted as a distance at 25° C.

However, using the concept of "virtual distance" (where $d_i$ values are scaled by TCD) is often useful and this can be implemented in certain embodiments. Furthermore, both the expansion and stiffness changes create a greater $\tau_i$ at higher temperature and a smaller $\tau_i$ at lower temperatures, so one coefficient is sufficient to reflect their combined result.

The time delays and phase shifting that make sensing possible are accomplished while the signal is in its acoustic form (i.e., a SAW), however, changes in these parameters are also observed directly in the RF wave received back at the interrogating transceiver 10 of FIG. 1.

The sensing capabilities of a PWSAW are based on differential delays of the echoes from the various RAs (in particular the echoes from adjacent RAs), rather than the absolute delay from any one RA or from a group of RAs. If this were not the case, the sensors could be made with a single RA and the time delay would be measured as precisely as possible in order to detect changes in $V_P$. However, this technique does not yield the precision that can be achieved with multiple RAs.

Returning to FIG. 1, the PWSAW sensor 8 comprises the various metal electrodes (IDT and RAs) that are deposited on a small piezoelectric substrate using standard semiconductor fabrication techniques. In one application the substrate is about 12 mm×2 mm. As described above, these metal electrodes launch, reflect and receive the surface acoustic waves (SAWS).

Note that the creation of a SAW wave by the IDT and the reflection back from the RA structures on the device are totally passive processes similar to a mirror reflecting light, except that the signal is at RF frequencies rather than visible light frequencies. Due to properties of the piezoelectric substrate, conditions of interest in the environment at the sensor create predictable variations in the echo signal produced by a PWSAW device. Thus allowing the SAW device to function as a sensor.

The SAW wave velocity, $V_p$, on the piezoelectric substrate is about $1/100,000^{th}$ the speed of the RF wave traveling in free space. So the SAW device adds a significant delay (equivalent to a distance of several kilometers) to the signal before retransmitting the RF echo signal. This echo delay gives the RF transceiver 10 of FIG. 1 time to complete its transmission and switch to receive mode before echoes arrive from the SAW sensor.

Also, due to this relatively low velocity and the very high ultrasonic frequency (anywhere from 200 MHz to 2000 MHz can be used for sensing), the SAW wave has a wavelength of only a few microns (e.g., 3.8 μm for a 915 MHz wave on lithium-niobate) which allows it to interact with very small features on the substrate.

When several SAW sensors must be operated simultaneously, the sensors are encoded with various time delays that enable the receiving system (i.e., the receive and attendant processing components) to isolate and identify data from each individual sensor.

BRIEF DESCRIPTION OF THE FIGURES

The present invention can be more easily understood and the further advantages and uses thereof more readily apparent, when considered in view of the following detailed description when read in conjunction with the following figures. In accordance with common practice, the various described features are not drawn to scale, but are drawn to emphasize specific features relevant to the invention. Reference characters denote like elements throughout the figures and text.

FIG. 7 illustrates a SAW topology with four RAs spaced according to an MR spacing pattern.

FIG. 8 illustrates a SAW topology with four RAs spaced according to a unit-lag spacing pattern.

DETAILED DESCRIPTION OF THE INVENTION

Before describing in detail the SAW sensor device of the present invention, it should be observed that the present invention resides primarily in a novel and non-obvious combination of elements and steps. So as not to obscure the disclosure with details that will be readily apparent to those skilled in the art, certain conventional elements are presented with lesser detail, while the drawings and the specification describe in greater detail other elements and steps pertinent to understanding the invention.

The following embodiments are not intended to define limits of the structure or method of the invention, but only to provide exemplary constructions. The embodiments are permissive rather than mandatory and illustrative rather than exhaustive.

Figure 1:
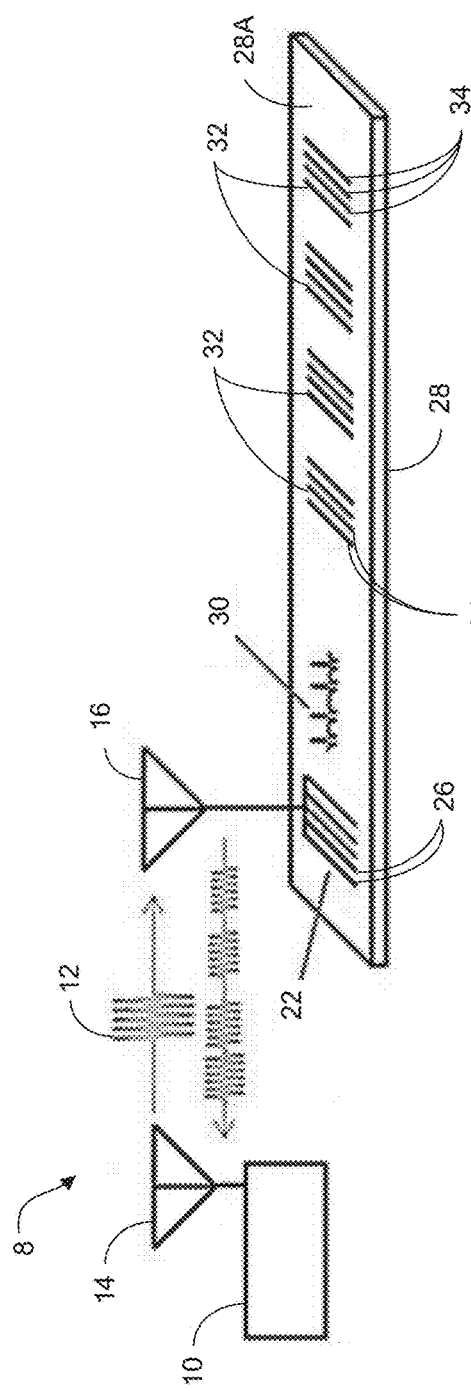
FIG. 1 illustrates a prior art remotely excited passive wireless SAW sensor device.
Figure 2:
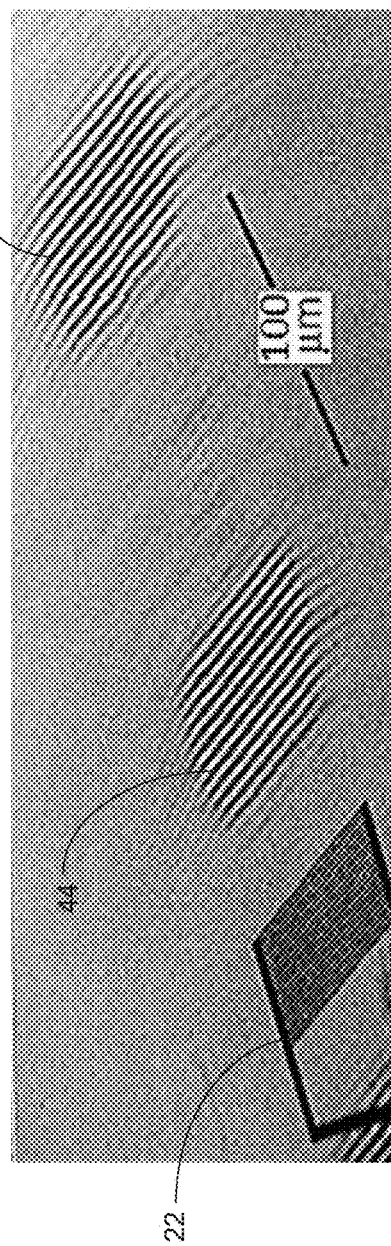
FIG. 2 illustrates SAWs propagating on a substrate according to the prior art.

Due to its symmetry, the IDT 22 of FIG. 1 in fact excites an acoustic wave in both directions, although only a single such acoustic wave is illustrated in FIG. 1. A bi-directional topology as illustrated in FIG. 4 provides the same time delays as the unidirectional device illustrated in FIG. 3, and makes use of the otherwise wasted back wave from the IDT. The RAs in FIG. 3 are spaced apart according to a 4 element minimum redundancy (MR) spacing as described further below.

Figure 3:
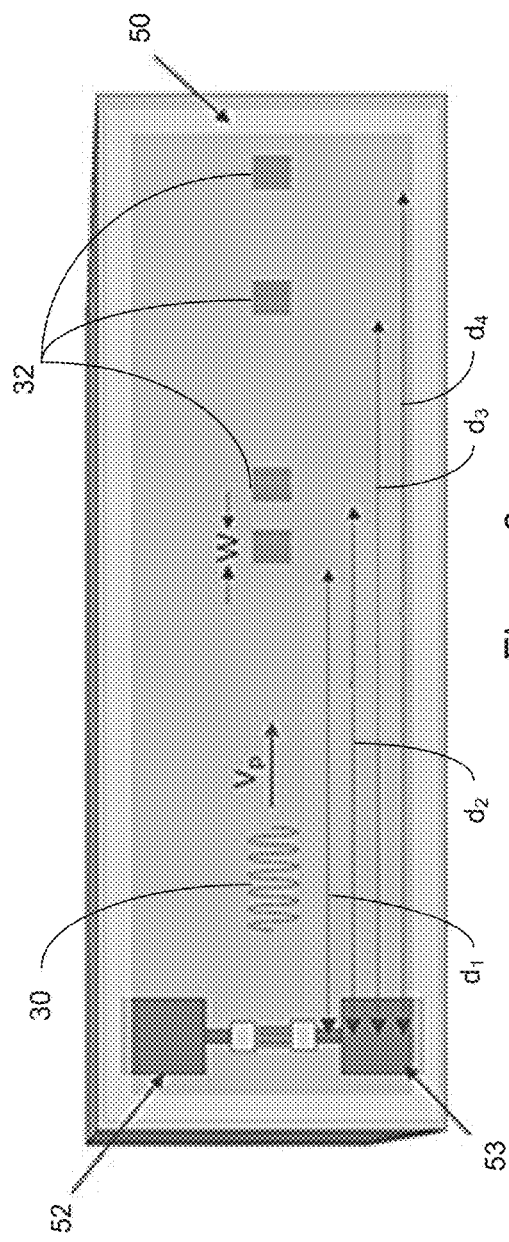
FIGS. 3 and 4 illustrate respective unidirectional and bi-directional SAW topologies with the reflector arrays spaced apart according to the present invention.
Figure 4:
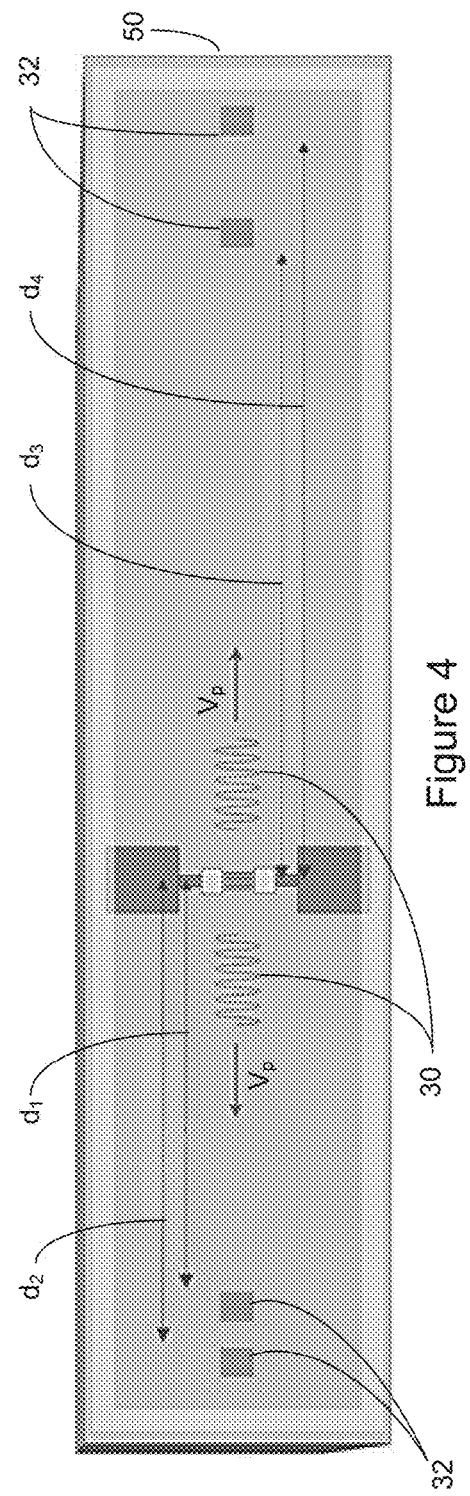

FIGS. 3 and 4 also illustrate several of the SAW device elements described above with reference to FIG. 1 and each additionally depicts distances $d_i$ from the IDT 22 to the various RA's 32. These figures also show a bordering absorber material 50 for absorbing the surface acoustic waves. Terminals or pads for connecting the antenna 16 of FIG. 1 are also shown and designated by reference numerals 52 and 53.

The bi-directional topology of FIG. 4 also reduces $2^{nd}$ and $3^{rd}$ order distortion from unwanted multiple reflections between RAs. The one drawback of this topology is that the substrate length must be nearly doubled.

From equations [3a] and [3b] above, it is clear that differential distances, such as the separation distances between RAs, will create differential delays ($\tau_{ij}=\tau_j-\tau_i$) which in turn create differential phase shifts ($\phi_{ij}=\phi_j-\phi_i$) between the $i^{th}$ and $j^{th}$ RAs. These phase shifts (time delays) are the parameters that yield the sensor measurements of interest.

The differential time delays and differential phase shifts are given by $$\tau_{ij}(T)=((d_j-d_i)/V_{P2})*(1+((T-25)*TCD)) \quad [4a]$$

$$\phi_{ij}(T)=2\pi f\tau_{ij}(T)=2\pi f((d_j-d_i)/V_{P2})*(1+((T-25)*TCD)) \quad [4b]$$

These differential distances or separation distances ($d_j-d_i$) of adjacent RAs are called "correlation distances," and the selection of these correlation distances is one subject of the current invention.

The parameter output of interest from the transceiver 10 (and associated processing components) of FIG. 1 is the fractional (i.e., percentage) change in the wave velocity, $V_p$, as derived from measured differential phases. And since the phase velocity is influenced by environmental conditions or effects (e.g., temperature and stresses/strains), these can be determined from changes in the wave velocity.

By using the physical constant TCD, a change in $V_P$ can be converted to "Apparent Temperature", or "ATmp", as expressed in degrees (either ° F. or ° C.), regardless whether the change is due to temperature or to stress/strain, or possibly a combination of both.

Since the temperature concept is more physically intuitive than a long dimensionless fraction, "ATmp" can be used to represent either the measured change in $V_p$ (i.e., the output of the measurement system) or the actual change in the environment that caused the measured value $V_p$ to change.

The relative time delay between echoes from any pair of RAs on a SAW device depends on the wave velocity, $V_p$, and on the distance between RAs ($d_j-d_i$) as shown in Equation [4a]. As the temperature of the substrate changes, the wave velocity changes with a ratio of TCD ppm/° C., which changes the delay, $\tau_i$, inversely as described by Equations [1a] and [1b]. But the wave velocity only changes tens of parts-per-million (ppm) per degree Celsius. So in order to precisely detect delay shifts both the amplitude and phase of the echo signal are used, significantly increasing the measurement sensitivity, as compared to measuring only the time delay of the pulse peak or the time delay of the pulse edges in the received signal (i.e., looking only at amplitude-based elements of the echo signal).

RA PLACEMENT: The sensitivity of a sensor device to changes in $V_p$ is determined by the longest correlation distance (also referred to as the maximum correlation distance) on the device, which is the separation distance between the two farthest RAs. It is therefore desirable to separate the RAs as much as possible.

The shortest correlation distance (separation between the two closest RAs) is selected to avoid a phase ambiguity that would otherwise make the sensed parameters ambiguous. Phase ambiguity occurs because the signal phase repeats each 360 degrees (or $2\pi$ radians), making it impossible, for instance, to distinguish a 370-degree shift from a 10-degree shift.

Thus this shortest correlation distance, also referred to as a unit-lag distance, is chosen by the device designer to provide something less than $2\pi$ radians (i.e., 360 degrees) of differential phase shift over the range of conditions to be measured. For instance, if temperature is the parameter of interest, the unit-lag distance is selected to provide less than $2\pi$ radians of phase shift between the lowest and highest operating temperatures.

With the shortest correlation distance referred to as the unit-lag distance, the longest correlation distance is also referred to as the N-lag distance, where lag in both cases refers to the time delay caused by these physical separations. The maximum correlation distance is in essence simply N times the unit-lag distance. Or conversely, N=(maximum correlation distance)÷(unit-lag distance). Thus the term "N-Lag."

If too many RAs are used to fill in the distance between the first RA and the last RA, the signal becomes too weak by the time it reaches the last RA, which reduces the sensor's useful interrogation range, i.e., the distance between the transceiver 10 and the sensor 8 of FIG. 1.

The present invention thus teaches how to fill the N-lag distance with a minimum number of RAs spaced at the unit-lag distance or a multiple of the unit-lag distance.

To complete the SAW sensor design the N-Lag distance is populated by M elements (i.e., by M RAs).

The maximum correlation distance ($d_M-d_1$) (the distance between the $m^{th}$ RA and the first RA) (and also referred to as the N-lag distance) defines the sensitivity of echo phase to changes in ATmp (i.e., either temperature or stress/strain). Using Equation [4b], the phase of echoes from the farthest separated RAs can be computed first for one temperature (assuming no strain) then at a temperature that varies slightly ($\Delta T$) from the first, where $\Delta T$ represents the desired accuracy or resolution of the system.

If the proposed resolution is to be achievable, this computed phase difference must be detectable by the electronics and the processing system provided in the transceiver. If it is not, the value of N needs to be increased and the phases recomputed for this longer correlation distance.

However, note that the accuracy of the processing electronics depends on several factors beyond the scope of this discussion, such as transmitted power, receiver sensitivity, number of bits in the digitizer, sophistication of the processing algorithms, etc. But once this accuracy value is known the N-Lag correlation distance can be specified. Suffice it to say that phase measurements finer than a few degrees (or about 0.05 radians) are very challenging for an RF processing system.

To fill the N-lag pattern with M RAs, various Minimum Redundancy (MR) sequences ideally will provide patterns with one pair of RAs separated by a distance of 1-unit ($L_1$), one pair separated by a distance of 2-units ($L_2$), and on up to a pair separated by the N-Lag distance ($L_N$).

The ideal RA pattern uses only one pair of RAs to provide each correlation distance. But in other embodiments, more than one instance of any separation distance $L_i$ can still be considered minimum redundancy if there are no "zero-redundancy" patterns available for the same values of N and M. Thus such patterns can be useful and are covered under the spirit of this invention. But in general minimum redundancy sequences will provide zero-redundancy of separation distances. For the purposes of this description, these patterns apply to separations in distance or time, which are made equivalent by the mechanism described by Equations [1a] and [1b].

THREE-ELEMENT MR SEQUENCES FOR PLACEMENT OF THREEE RAs: For a sensor with three RAs, there is only one MR sequence (two MR sequences when this same sequence in reverse order is included), and it distributes the three RAs among four 1-unit (unit-lag) time slots.

Figure 5:
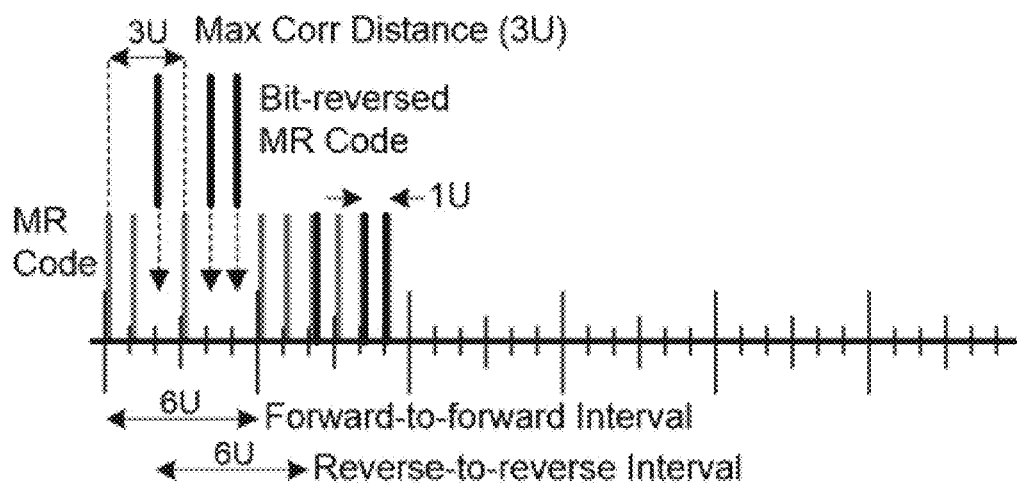
FIG. 5 illustrates interleaving of a three-element (three RAs) minimum redundancy code and its bit reversed version.

To describe the placement of the RAs MR binary codes are used with a "1" indicating "RA present" and "0" indicating "RA absent." See FIG. 5.

Binary value: 1-1-0-1 (or in bit reversed order: 1-0-1-1).

Decimal value: 11d or with bit reversal: 13d (where the ending "d" indicates a decimal value).

The sequence indicated in FIG. 5 by the RA's shown with a bold line weight is the result of bit reversing the standard line weight RA sequence. By alternating the bit-reversed and non-reversed patterns, all lag time slots are occupied, which makes maximum use of the available substrate length.

FIG. 5 also indicates the maximum correlation distance of 3 U (unit-lag distance) as the distance between the first and last RA in a three element MR sequence. The 6 U forward-to-forward interval is also shown for both the forward MR sequence and the reverse MR sequence.

Note that by choosing the maximum number of independent codes required (i.e., the number of simultaneously interrogated sensors) one can specify the required substrate length.

For SAW sensors, the 3-element MR sequence provides a maximum correlation distance of 3 units (3 U), versus only 2 units using a 3-element unit-lag code (2 units between three elements). This modest increase in correlation distance ($L_N$) of one unit represents a 50% improvement in the sensitivity of the sensor.

Once the initial time delay ($\tau 1$) and the RA spacing have been specified, we refer to the resulting RA pattern and the resulting time delays as the sensor's code, as in the "Code 1" or "Code 4" sensor.

The 3-element sequence is almost a trivial case of the MR sequences, but provides a simple illustration of sensor encoding and placement of the RAs, the resulting performance improvement, and the concept of interleaving. As shown in FIG. 5, by alternating the bit-reversed and non-reversed MR sequences, one sensor's code can be over-lapped with other sensors' codes, albeit with some care concerning time delay changes over the full temperature range. This overlapping is referred to herein as "interleaving of codes".

The system designer must consider how much t will vary by two sensors that use adjacent code delays when one sensor is experiencing a much higher or lower ATmp than the other sensor. Temperature or strain differences will shift the time delay of all RA echoes on each sensor by the factor TCD as shown in Equation [3a]. So spacing must be chosen such that echoes from one sensor do not overlap echoes from another sensor when the two are at their maximum possible difference in ATmp. Also the change in delay is greater as $d_i$ (the distance out from the IDT) increases, which is apparent from Equations [1a] and [1b].

FOUR-ELEMENT MR SEQUENCE FOR PLACEMENT OF FOUR RAs: For a sensor with four RAs, there is also only one MR sequence (two MR sequences including this same sequence in reverse order), and it places the four RAs into seven 1-unit delay time slots, thus providing a maximum correlation distance of 6-units.

Binary value: 1-0-1-0-0-1-1 (or in bit reversed order: 1-1-0-0-1-0-1).

Decimal value: 83d or with bit reversal: 101d

Figure 6A:
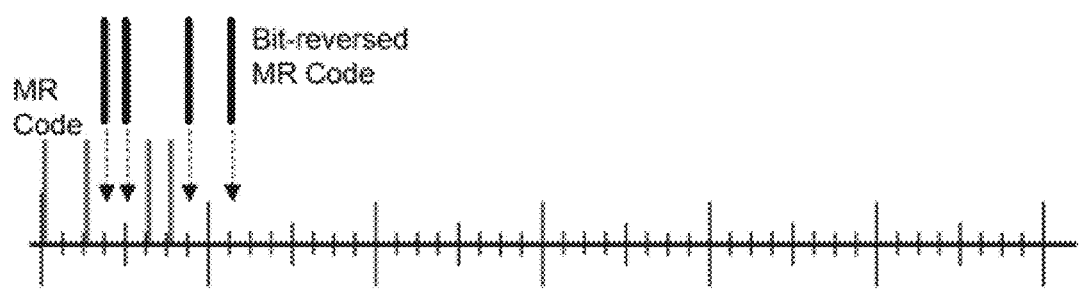
FIGS. 6A and 6B illustrate a minimum redundancy code for a four-element (four RAs) code and interleaving of a four-element minimum redundancy code and its bit reversed version.

The 4-element MR sequence and its reverse sequence is shown in FIG. 6A.

Figure 6B:
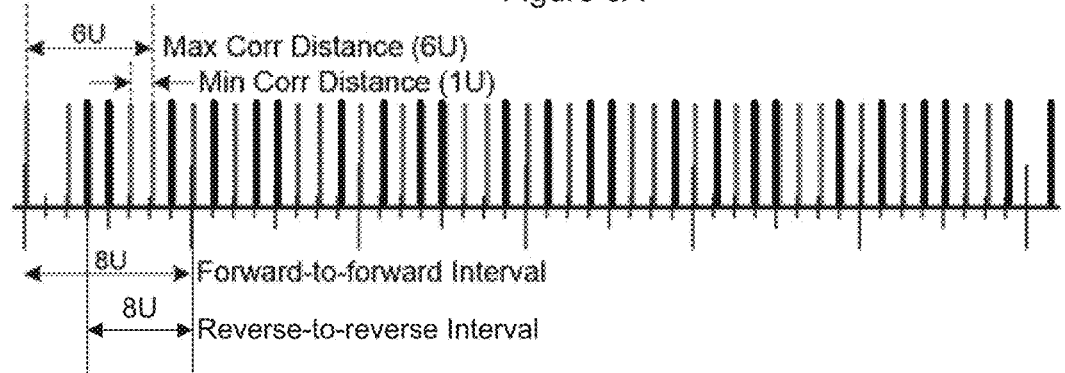

Like the 3-element MR sequence, the 4-element sequence also allows optimal interleaving as shown in FIG. 6B. In FIG. 6B the pattern is repeated many times to show how the codes consume the available delay time provided by a substrate of finite length.

The unit-lag distance is typically much greater than the width (W) of an RA (see FIG. 7 where the width W is indicated). There will be an open space between RAs even at the 1-unit separation distance as illustrated by the layout shown in FIGS. 7 and 8, which compares a 4-element unit-lag pattern (FIG. 8) to a 4-element MR pattern (FIG. 7).

The MR pattern of FIG. 7 provides one pair of RAs separated by a distance of 1-unit ($L_1$), one pair separated by a distance of 2-units ($L_2$), one pair separated by a distance of 3-units ($L_3$) and continuing up to a pair separated by the N-Lag distance ($L_N$) where N=6. Certain ones of the distances are labeled, but careful study of the 4-element MR pattern reveals the presence of the $L_4$ and $L_5$ distances, which are not labeled.

The parameter W is determined by the acoustic wavelength, the type of RA (i.e., shorted or open ended electrodes) and the number of electrodes in each RA. However, irrespective of the number of electrodes that comprise one RA, the echoes produced by the individual electrodes are coherent with each other and can therefore be considered a single reflection located at the centroid of the RA.

Figure 9:
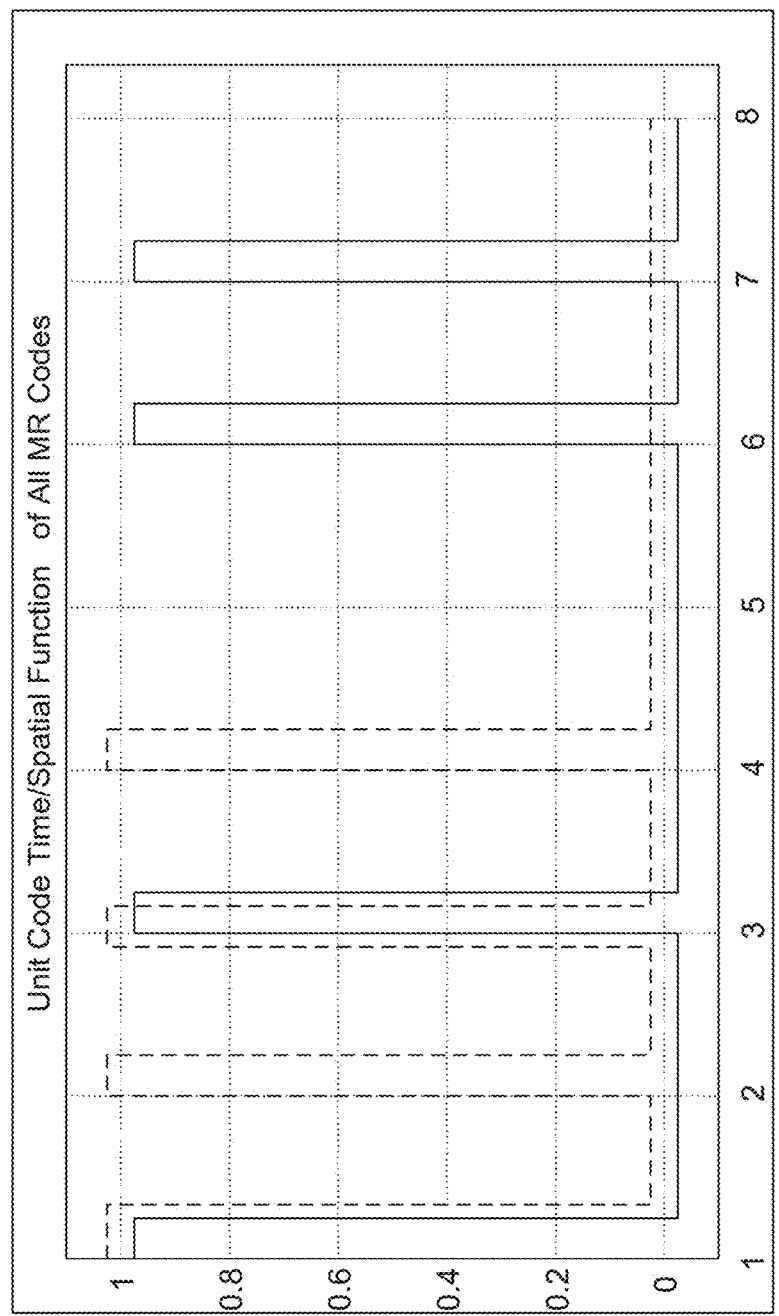
FIG. 9 illustrates echoes from a 4-of-7 MR code (solid lines) and a unit-lag code (dashed lines).

FIG. 9 illustrates the response from a four-element unit-lag sequence (dashed line) (i.e., four RAs spaced at the unit-lag separation distance) and the response from a 4-of-7 MR code spacing, with the dashed lines offset slightly from the solid lines for visibility. The unit-lag pattern provides a maximum correlation distance of three units. The 4-of-7 MR sequence provides all correlation distances from 1 to 6 and a maximum correlation distance of six.

FIVE-ELEMENT MR SEQUENCE FOR SPACING OF FIVE RAs: There are no 5-element MR patterns that provide exactly one RA pair per lag value using five RAs, so any sequence that provides a small number of duplicate lag values (e.g., 2579d or 3205d) can be used if the use of a 4 or 6 element sequence is impractical.

SIX-ELEMENT MR SEQUENCE FOR SPACING OF SIX RAs: There are three unique sequences (six including the bit reversed sequences) for placing six RAs into eighteen unit-lag time slots.

MR Sequence 1
  Binary Value: 1-1-0-0-1-0-0-0-0-0-1-0-1-0-0-0-0-1 (bit reversed 1-0-0-0-0-1-0-1-0-0-0-0-1-0-0-1-1)
  Decimal Value: 136211d (bit reversal 204961d)

MR Sequence 2
  Binary Value: 1-1-0-0-0-0-0-1-0-0-1-0-1-0-0-0-0-1 (bit reversed 1-0-0-0-1-0-1-0-0-1-0-0-0-0-0-0-1-1)
  Decimal Value: 141571d (bit reversal 197201d)

MR Sequence 3
  Binary Value: 1-0-1-0-0-0-0-1-0-0-0-0-1-0-0-1-1 (bit reversed 1-1-0-0-1-0-0-0-0-1-0-0-0-0-1-0-1)
  Decimal Value: 204933d (bit reversal: 164883d)

The various MR sequences described herein for placement of the RAs are also referred to as "3-of-4" (for three RAs), "4-of-7" (for four RAs), or "6-of-18" (for six RAs).

As the MR sequences become longer their performance improvement over the unit-lag spaced arrays becomes more dramatic. The 6-of-18 MR sequence covers 17-units of correlation distance compared to only a 5-unit distance for a six element unit-lag sequence. For SAW sensors this improves measurement sensitivity by a factor of about 3.4. For example, if the 1-unit-lag spacing can achieve a temperature resolution of 1.0° C., then the 6-of-18 can provide 0.294° C. resolution.

Since a significant amount of the input signal energy is lost by the time the incident SAW reaches the sixth RA, in one embodiment the RAs are split into two groups creating a bi-directional device as shown in FIG. 4.

Since the IDT is symmetrical it launches the same SAW wave in both the +x and −x direction. Launching bi-directional waves and therefore dividing the RAs into two groups (of two RAs in each group) avoids wasting energy in the "back pulse." Also, the echoes from the farthest RAs are much stronger in a bi-directional embodiment as compared with the echoes from a unidirectional embodiment where the incident energy must pass through M−1 RAs before reaching the last RA. Additionally, the bi-directional topology generates fewer unwanted $2^{nd}$ and $3^{rd}$ order effects from waves reflecting back and forth between RAs before returning to the IDT. Of course all these bene/fits come at the expense of nearly doubling the device length.

It is typically possible for the echo time delay (i.e., $\tau_i$, the delay of the echo from the first RA) to shift by more than a unit-lag distance over the range of ATmp values to be sensed. Some signal synchronization should be implemented in the processing of the received echo signal. This synchronization task greatly increases interest in the shape of the auto-correlation function (or ACF, which is the correlation of any function with itself) that is produced by the RA spacing pattern; the MR sequences have very good ACF properties as described herein.

As described, the location/spacing of RAs on a particular sensor specifies how much delay the transmitted signal will experience before the echo signals are re-radiated. If the transmitted signal is a perfect impulse, $\delta(t)$ (sometimes called a Dirac delta function, which has one unit of power but zero width), the delay pattern of the returned echo signal, r(t), would be a "picture" of the RA placement on the substrate. The function h(t) that describes this pattern is referred to as the impulse response of the RAs, because the r(t) returned echo signal is the convolution of the transmitted signal or incident SAW s(t), with the impulse response of the sensor, h(t). If s(t) is a single point with unit amplitude, that is, s(t)=δ(t), then it simply replicates (or scans, like a fax machine) h(t) into the function r(t).

The sensors can be interrogated by a variety of wideband transmitter signals (i.e., the incident SAW), but the selection of transmitted signal is not germane to the present invention. It is possible to remove the characteristics of the transmitted interrogation or incident signal, s(t), from the received echo signal, r(t), leaving only the sensor's impulse response, h(t). However, the amplitude and initial time delay (due to the RF propagation delay) for r(t) can change, therefore after converting the transmitted signal to a Dirac delta function, the remaining component that resembles h(t) is referred to as r'(t), since it may vary from the theoretical h(t) in amplitude and initial delay.

The discrete sampled data representation for these signals will be used from this point forward, so the h(t) becomes h[n], the digitally sampled receiver signal becomes r[n], or after removing the transmitted signal we get r'[n], where n is the sample number for digitizer samples taken at a rate of fs, the sampling frequency.

Also note that the concept for δ(t) is simplified since δ[n] is now simply a function that has a value of 1 at n=0 and zero elsewhere. This discrete time version of the Dirac delta function is called the Kronecker delta function, δ[n].

From Equations [3] and [4] above, it is apparent that the function h[n] changes according to the current ATmp at the sensor; and by determining how much h[n] has changed, the transceiver/processing system can determine the current temperature at the sensor.

To account for the temperature dependent changes in h[n], a set of functions, h[T,n], is defined to represent the expected sensor responses at different values of ATmp. These can be pre-computed from a model using the known RA placement and substrate characteristics, or can be measured using actual sensors. In either case the h[T,n] functions can be stored in the transceiver since they do not change over time. The detection processing involves correlating the h[T,n] functions with the actual received h[n] to see which value of T best describes the current state of the sensor. Therefore, particularly at the correct value of ATmp (call it $T_c$), the stored function $h[T_c,n]$, and the function h[n] extracted from the received signal (now called r'[n]) are nearly identical. The only differences between them being that the amplitude of r'[n] can vary and initial time offset of r'[n] will include a delay due to RF propagation. Therefore, since the detection process involves correlating the received function, r'[n], with the expected functions, h[T,n], the result is essentially an ACF of the sensor's impulse response with itself. This is why the ACF of the MR sequences is of interest.

When the transceiver is initially attempting to locate the echo signal from a particular sensor it must compensate for:
  1. RF delay (about 2 ns per 1 foot of distance between the transceiver and sensor)
  2. Delay shifts caused by the apparent temperature or strain at the sensor.
  3. The large differences in echo delay due to the placement of RAs on the sensor, but these are known and should not require the transceiver to search for them.

By examining FIGS. 5 and 6B it is apparent that only two unique MR sequences, or patterns, are used for a whole set of sensors, and the various sensor "codes" just involve changing the time offset ($\tau_1$) of the first echo from each sensor. Furthermore the integer multiples of phase (the x times P ambiguity) mean that with careful placement the h[T,n] function for various sensors can have the same phase response, so even though the h[T,n] functions are complex there still only needs to be two unique functions stored.

Also, we should define a different set of h[T,n] functions for each sensor, represented as h[q,T,n] where q is the sensor number; but since it need not be implemented that way we will ignore the q term. The notation for the remainder of this description will generally use just h[T,n], and the need for adding the different initial time delays for different sensor codes is understood.

Figure 11:
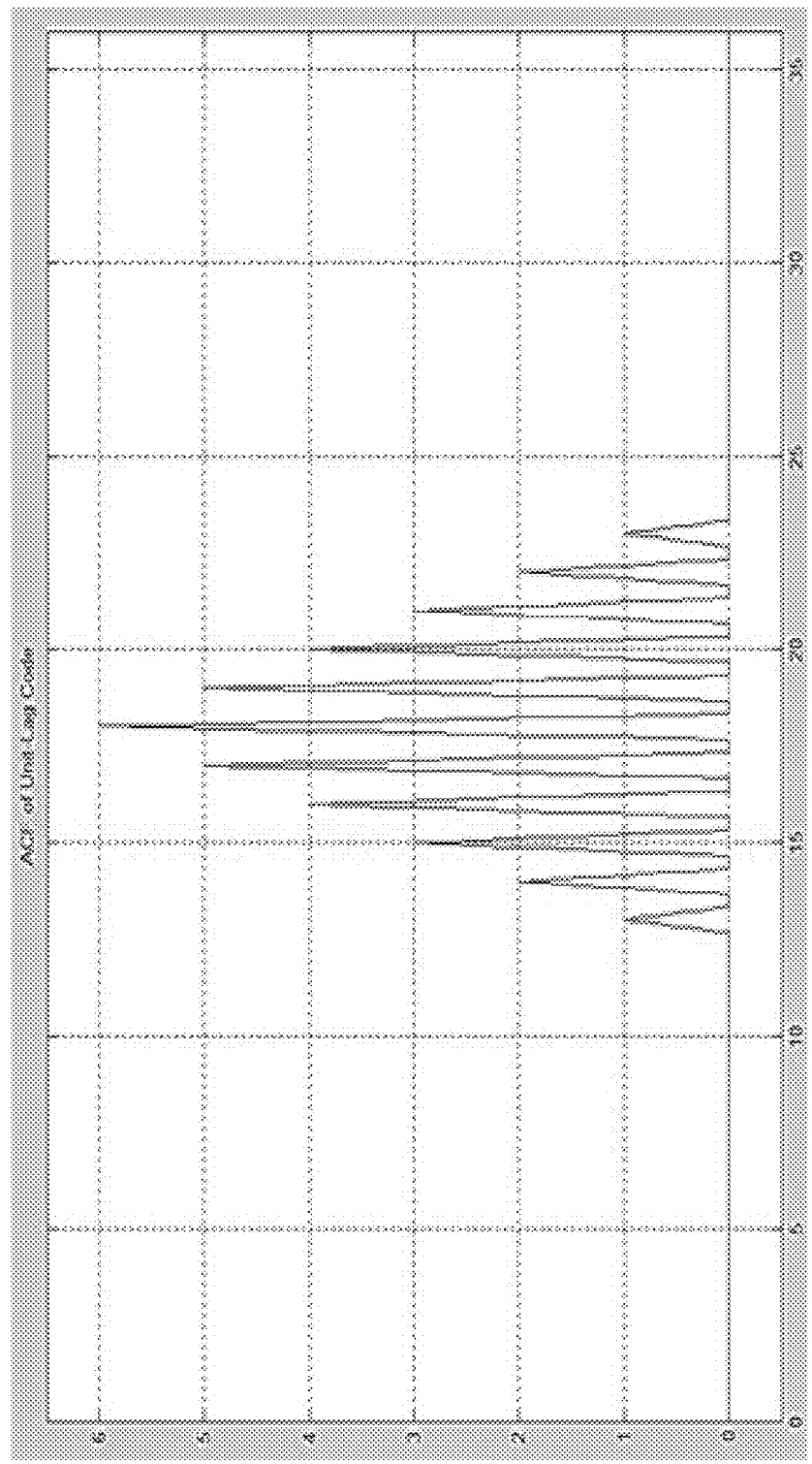
Figure 13:
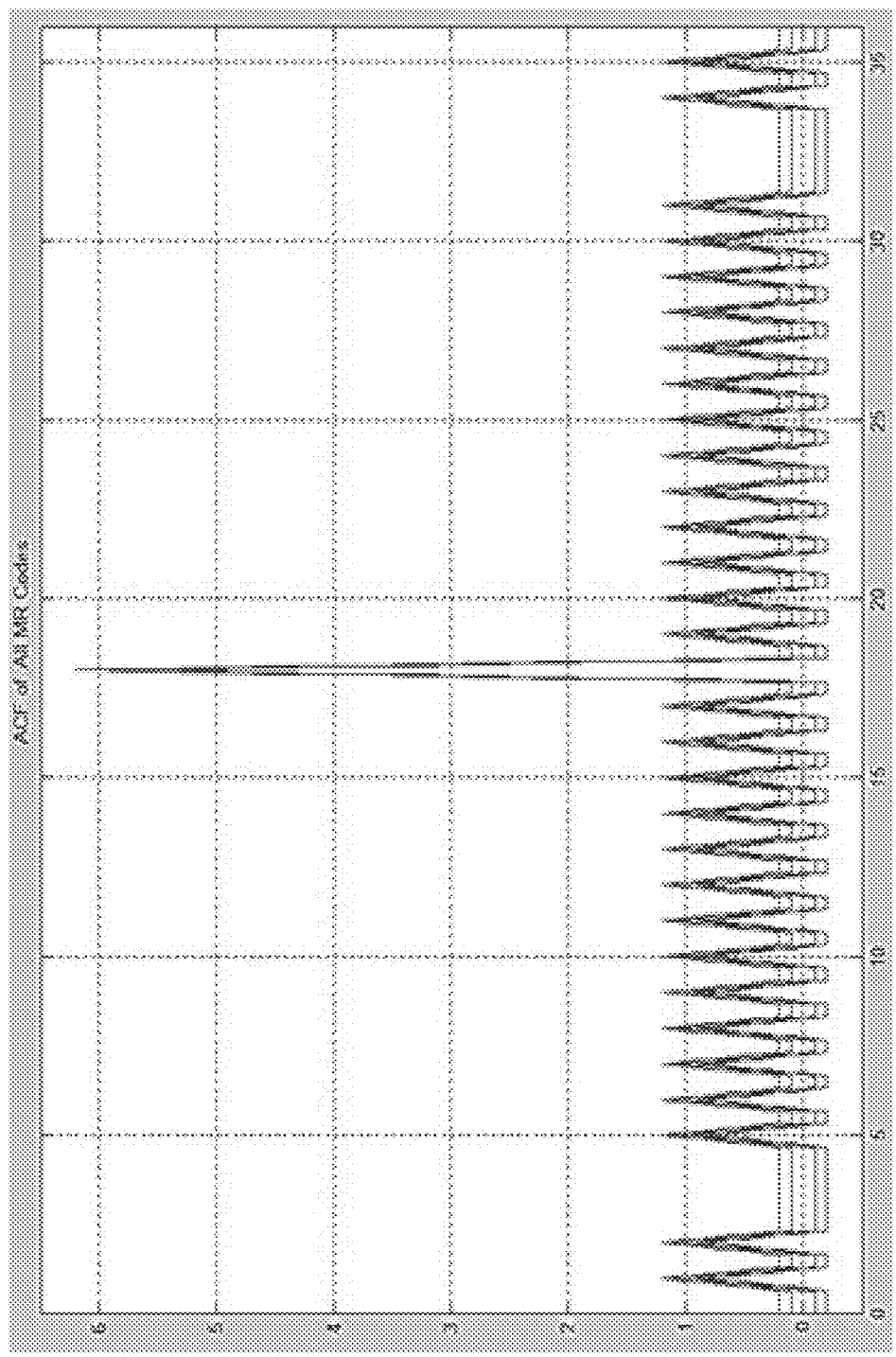
Figure 14:
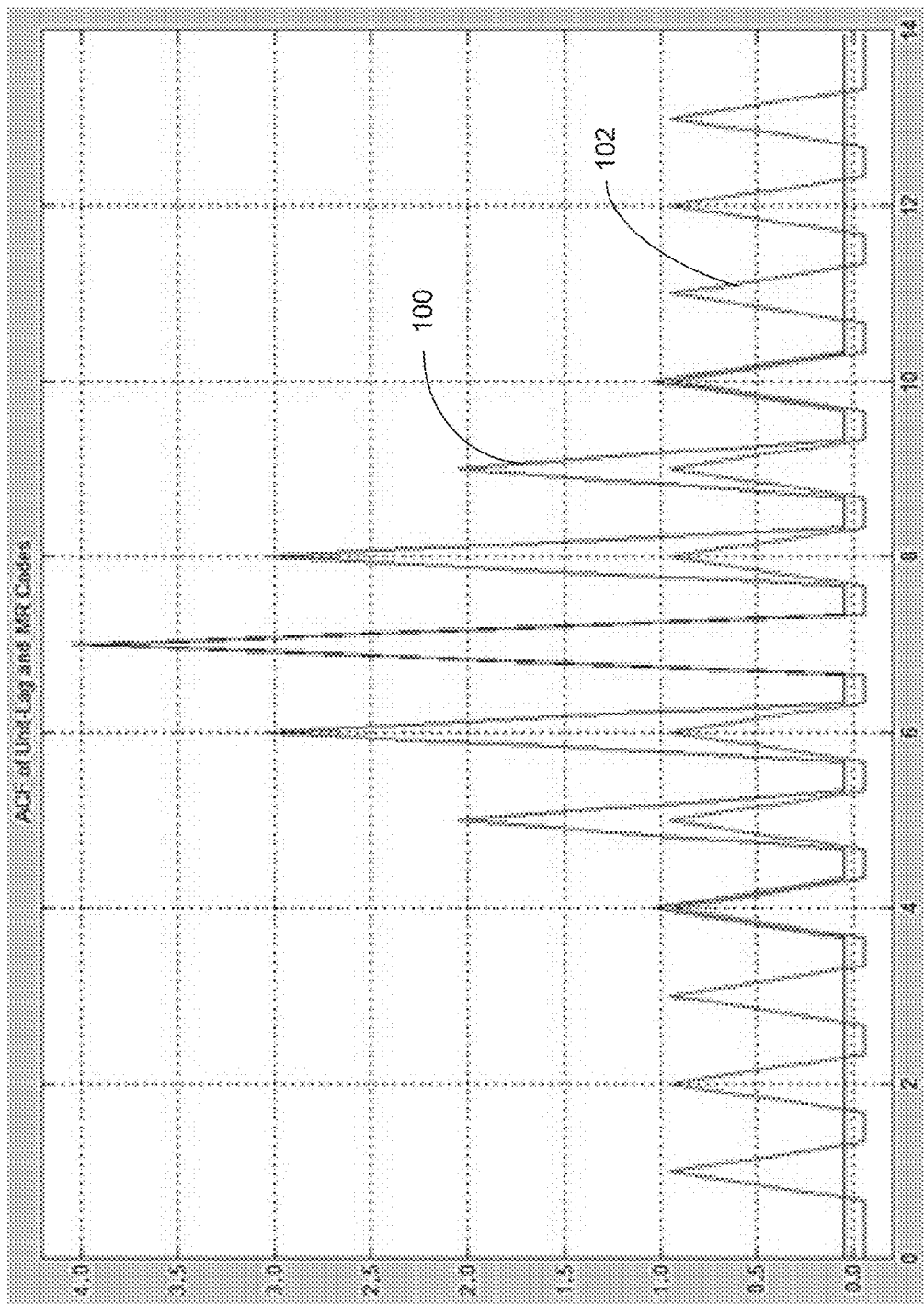
FIG. 14 compares the auto-correlation function for a 4-element RA with unit-lag spacing and the auto-correlation function of a 4-of-7 MR spacing RA.

For perspective, consider a transceiver that samples received echoes at 400 million samples per second (400 MSps, or 2.5 ns per sample) and a sensor built on lithium-niobate with its first RA at 7 mm from the IDT. At 25° C. the two-way propagation velocity ($V_{p2}$) is 1.74 µm/ns, and the TCD is 94 ppm/° C., so the echo delay ($\tau_1$) from RA1 is 4.023 µs at 25° C. and would be 4.051 µs at 100° C. This is a difference of 28 ns, which is more than 11 digital samples in the sampled data record, r[n], or in r'[n]. Add to this an uncertainty of +/−50 ft. in distance from the transceiver, and this sensor echo could arrive at any time within +/−128 ns (about +/−51 digital samples) from the delay time expected for this sensor at some nominal temperature and distance. Also note that the unit-lag separation distance between correlation peaks shown in FIGS. 11, 13 and 14 are typically in the range of 20 to 40 ns. So with delay uncertainty of +/−128 ns, the transceiver must synchronize to the received echo signal, which means locate its starting and ending location in the sampled data record, r[n] or r'[n]. Also note that this amount of spacing between codes from different sensors may be needed to avoid overlapping.

The plots below, FIGS. 10 through 14 show that especially in the presence of noise and interference (not included in the figures) the MR sequences have excellent ACF properties compared to unit-lag spacing patterns. This is because the ratio of the peak amplitude of the ACF to the nearest sidelobe is much greater for the MR patterns. Sidelobes of unit-lag patterns fall off gradually in amplitude with each successive sidelobe making the main peak less distinct from the sidelobe peaks. The prominence of the central peak in an MR sequence helps prevent errors when selecting the peak value out of more than 2000 samples in each received signal array, and from among all the peaks resulting from correlating the functions h[T,n] where there is typically on the order of 100 values for T.

Figure 10:
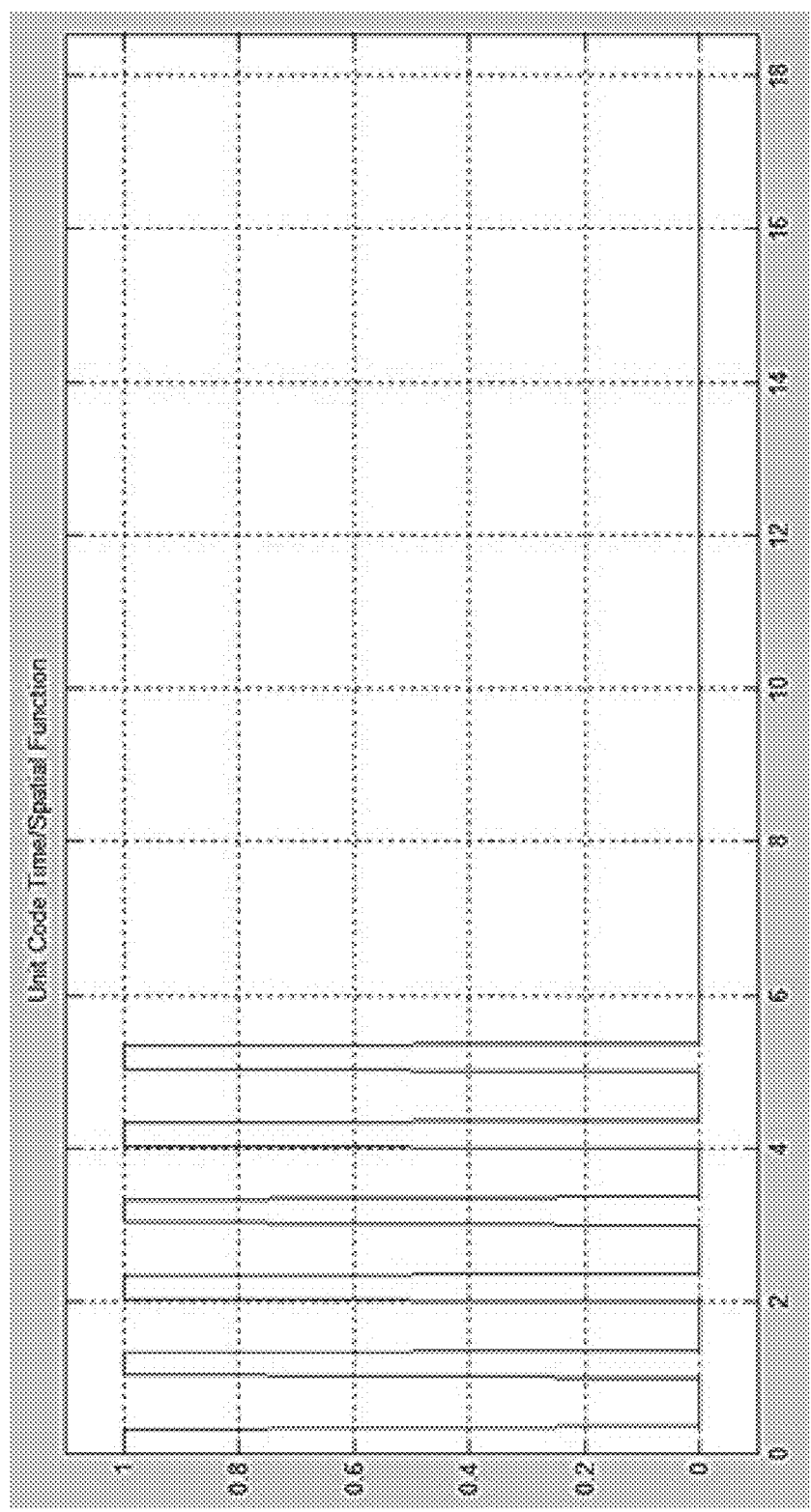
FIGS. 10 and 11 illustrate the delay spacing and auto-correlation function (ACF), respectively, for a 6-element unit-lag RA spacing pattern.

FIGS. 10 and 11 present a baseline by showing the delay spacing and ACF, respectively, for a 6-element unit-lag RA spacing pattern. Note the close spacing and gradual amplitude reduction of the unit-lag ACF sidelobes.

Figure 12:
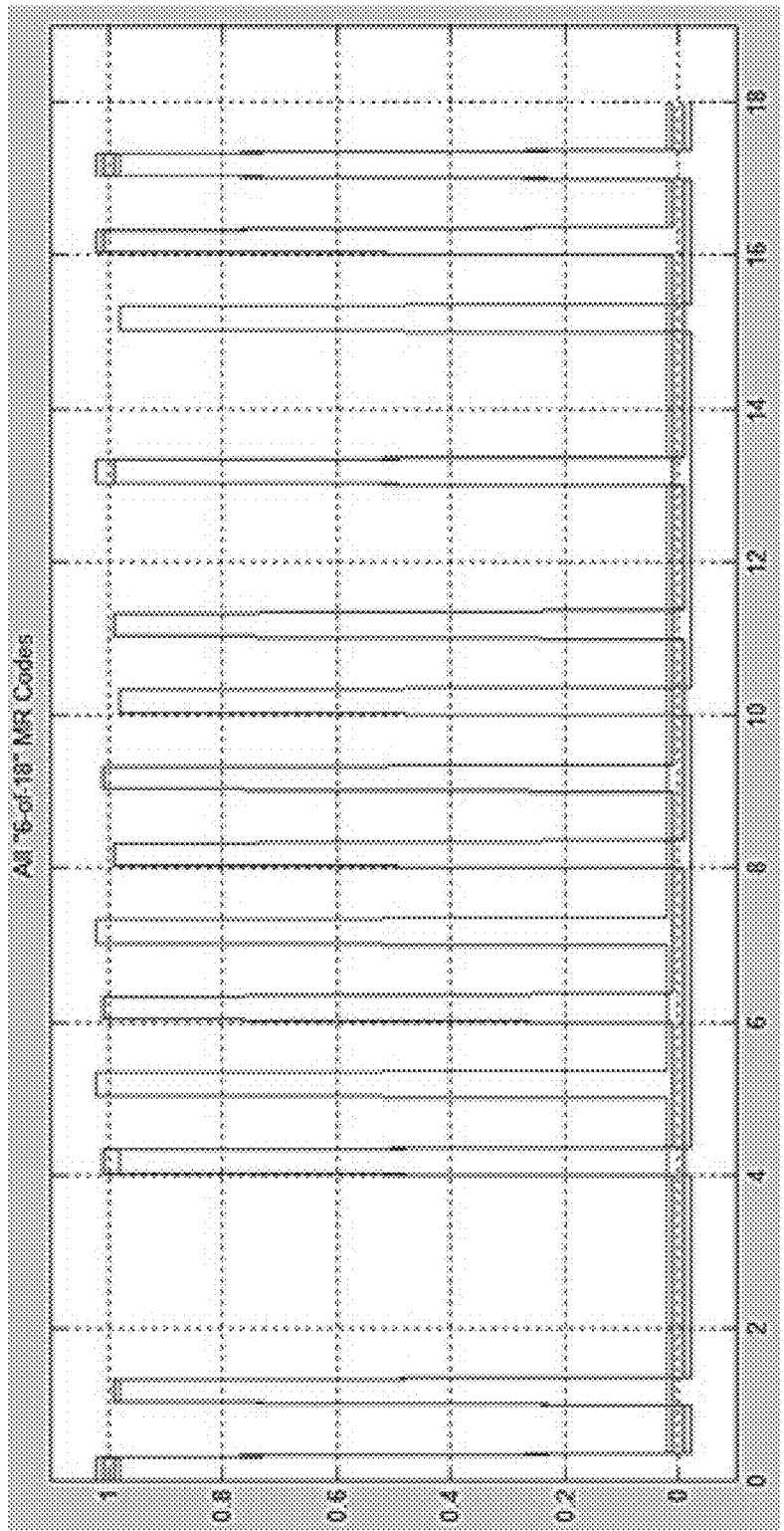
FIGS. 12 and 13 illustrate the overlaid time functions and overlaid autocorrelation functions, respectively, for four of the 6-of-18 MR codes.

FIGS. 12 and 13 show the overlaid time functions and overlaid autocorrelation functions (ACF), respectively, for four of the 6-of-18 MR codes set forth above. Note the more prominent ACF peak in the MR code sequence as compared with the unit-lag ACF peak in FIG. 11.

FIG. 14 overlays the ACF of the unit-lag sequence 100 and the ACF of the MR sequence 102 for the simpler 4-element case. The unit-lag ACF shows a triangular fall-off of successive side-lobes, while the side lobes of the MR sequence ACF show a sudden drop to a relatively low value. The peak-to-sidelobe ratio increases with increased sequence length.

Signal Processing to Detect Changes in Vp.

Figure 15:
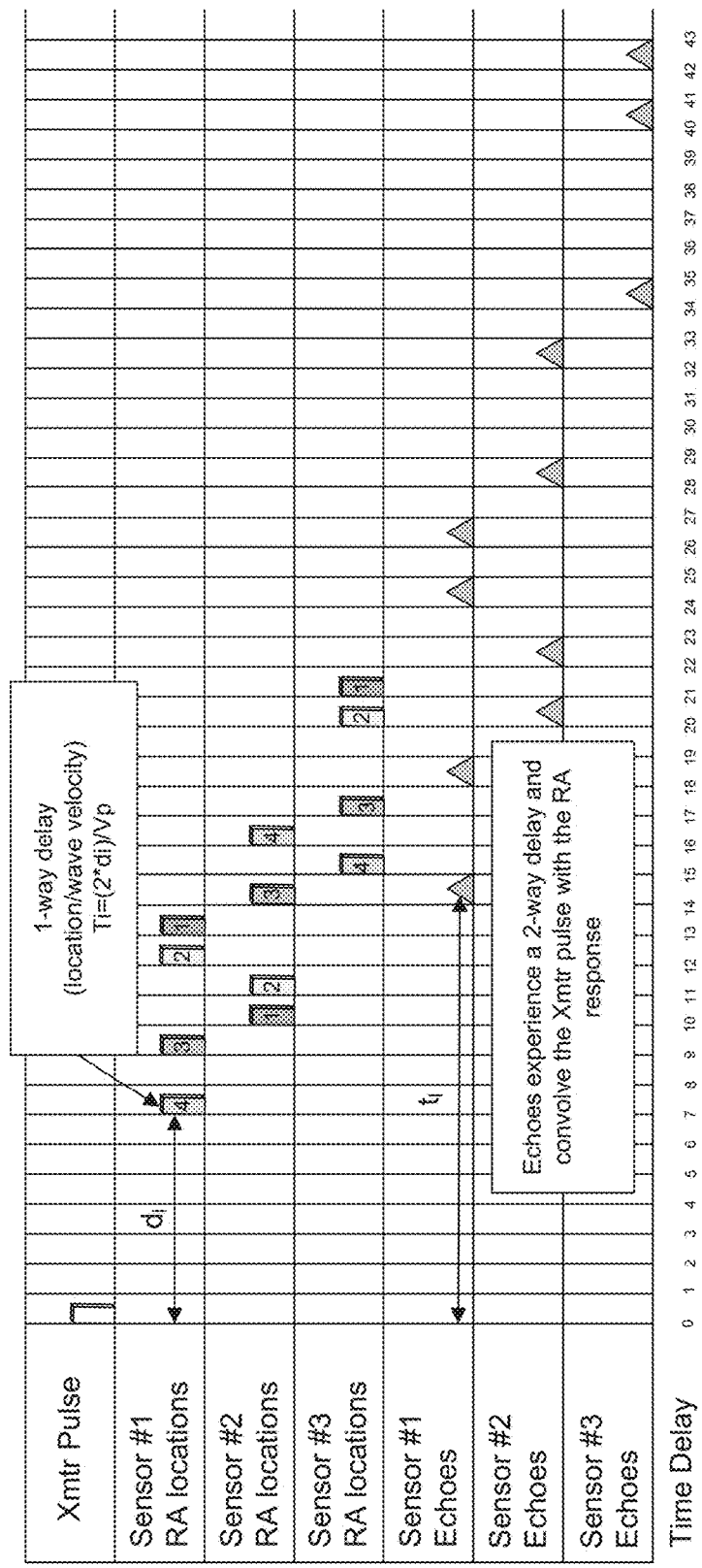
FIG. 15 illustrates the delay timing in terms of location of RAs relative to the IDT for a 4-of-7 MR coded reflector array.

With reference to FIG. 15, the physical location of reflector arrays (RAs) in row 2 thru 4 determines echo delays from each of three sensors as dictated by Equations [1a] and [1b]. The reflected signals shown (blue triangles) are the convolution of the rectangular "radar" pulse (shown in row 1) with the impulse response of each RA. In words, the leading edge of the incident pulse reflects from the first finger of an RA, then from the $2^{nd}$ finger, $3^{rd}$, etc., making a larger and larger echo amplitude. The echo peaks when the transmitted pulse is engaging all fingers of the RA simultaneously. As the pulse leaves the back of the RA, the $1^{st}$ finger stops reflecting, then the $2^{nd}$ etc., and the amplitude drops back to zero. So the triangular shape is expected.

FIG. 15 shows the application of the 4-of-7 MR code to a SAW sensor. When excited by a unit impulse, δ(t), the sensor will echo back its impulse response, usually represented as h(t). The impulse response is basically a picture of the physical position and width of the RAs, where, because of the Equation 1 relationship, echoes from the RAs have the same time delay pattern ($\tau_i$) as the physical locations ($d_i$) of the RAs. The patterns shown in rows 2 thru 4 represent the physical locations (spatial function) of RAs for three different sensors.

However, if excited by a real signal, such as the rectangular "radar" pulse shown on row 1, the echo signals (lines 5 thru 7 of FIG. 15) are the convolution of the transmitted signal with each RA, with the time scale expanded to emphasize the effect of the two-way delay time. The blue triangles (lines 5 thru 7 of FIG. 15) represent the convolution of the incident rectangular pulse with the impulse response of the rectangular shaped RAs as dictated by Equation [5]. According to linear systems theory, for an input signal, s(t), the response, y(t), will be the convolution of that signal with h(t). A shorthand way of writing this is:

$$y(t)=s(t)*h(t)$$

or as a discrete time (i.e., sampled data) system $$y[n]=s[n]*h[n], \text{ where } t=n/f_s, f_s \text{ is the sample rate and } n \text{ is an integer,}$$

Adjusting to use the echo signal notation, the discrete-time convolution integral is:

$$r[n]=\Sigma_{k=-N}^{(N-1)}s[k]h[n-k] \qquad [5]$$

It is clear to see that if s[n] is a unit impulse δ[n], then y[n]=h[n], since s[k] only has a value when k=0.

Rows 2 thru 4 of FIG. 15 represent the physical distances of RAs on the sensors or by replacing $d_i$ with t (as in Equation [1a] or [1b]), it represents the sensor's time-domain impulse response. For this rectangular transmitter pulse shown, the next three rows (rows 5 thru 7) represent the echo signal produced by RAs on three different sensor devices that are spaced according to the 4-of-7 MR sequences. Note that in FIG. 15 each sensor is carefully encoded with three different initial time offsets (ti) to avoid overlapping the received signals. Each blue triangle represents the echo from one RA, and together (across the row) they represent the "expected" echo functions, r[n], for sensor #1, #2 and #3. After processing the received signals to remove the characteristics of the transmitted signal, the function r'[n] would lose the triangular effect and once again resemble the rectangular placement shown in row 2 thru 4, which is the impulse response for sensors #1, #2 and #3.

A few points to consider are that because the amplitude of the transmitted signal (as seen at the sensor) can vary greatly, the amplitude of the "recovered" function r'[n] also has a variable amplitude which is correctly represents these variable RF signal losses. Also, the initial time delay ($\tau_1$) in the function r'[n] will depend not only on the position of the first RA, but also on the distance between the sensor and the transceiver (i.e., it includes the RF propagation delay, while the stored impulse responses h[T,n] do not).

Although FIG. 15 gives an idea of what a physical received signal looks like, it is preferred to remove the transmitted signal's characteristics and work with just the processed received signal, r'[n], which is a function that very closely represents the sensor's impulse response, h[n].

For greater temperature resolution the h[T,n] functions can be annotated as h[k,n] where the temperature, T, is represented by k, and T=kΔT. However, to simplify notation assume ΔT=1° C. (or 1° F.), so T=k, which makes the notation (i.e., h[T,n]) more intuitive. Also, recall that there are actually a set of functions h[T,n] for each sensor, but since Q values are not stored for Q sensors, we will continue ignoring the index q in the functions h[q,T,n].

Now by correlating all of the functions h[T,n] with the received signal, r'[n], we can find which one produces the largest correlation peak; and thus determine the sensor ID and the ATmp value at the sensor location. Typically the functions h[T,n] are time reversed and conjugated to create a "Matched Filter", mf[T,n]. This conforms with the "Black Box" concept of linear systems theory where an input signal is convolved with the impulse response of the black box to produce an output signal, which can then be cascaded on to the next black box. This black box concept is also used by Equation [5] to generate the actual echo signal, and it is similar except that Equation [6] uses notation appropriate to processing the received signal.

$$CF[n]=\Sigma_{k=-N}^{(N-1)}r'[k]mf[n-k] \quad [6]$$

Equation [6] results in a "CF", or Correlation Function, since, due to variable amplitude and variable initial delay, r'[k] is not exactly equivalent to mf[n-k], so it is not an ACF. Although the equations [5] and [6] look very similar, the concept in the receiver processing is quite different from the concept of generating the echo signal from a real transmitted signal.

The generation of the echo signal (Equation 5) is a true black box (cascadable input-output) operation, in that it produces an output signal y[n] when given the transmitted signal, s[n] as input, and it doesn't matter if h[n] and s[n] are similar or resemble each other in any way. In contrast, the processing of the received echo signal is a true correlation, in that it is a measure of how much one signal looks like another (i.e., how much the received signal looks like each of the predicted signals, h[T,n]).

The MFs that represent the expected echo signals are the functions h[T,n] reversed in time and conjugated, but notice that the "-k" in the convolution integral of Equation [6] "re-reverses" the time axis, making the operation a correlation of the actual received h[n] (i.e., the function r'[n]) with the expected h[T,n] functions. When T=$T_c$, the current temperature at the sensor, Equation [6] convolves r'[n] with mf[$T_c$,n], which produces something like an ACF of h[$T_c$,n]; the difference being that the time offset in the correlation function (CF) produced accurately represents the RF propagation delay and its amplitude is linearly proportional to the amplitude of the received signal; both very nice features of the process. In other words, the normalized h[T,n] functions work equally well for signals with different initial delays (due to the RF propagation delay) and different amplitudes (also mostly of function of distance between transceiver and sensor).

To summarize the signal processing, the transceiver stores a set of precomputed matched filter functions, mf[T,n] or mf[k,n] from which the specific sensor codes h[q,T,n] are generated. The MF functions are derived from the h[q,T,n] functions by phase conjugation and time reversal according to:

$$mf[n]=h[-n]^* \text{ where}^*\text{indicates phase conjugation.}$$

Note that the MFs do not account for RF signal propagation delay so the processing in the transceiver must be capable of synchronizing r'[n] with h[T,n]. With the correct set of MFs stored onboard, the receiver first captures a digitized received echo signal, processes it to remove the transmitted signal, isolates the echo signal for each sensor, then correlates the received signals with each of a set of matched-filters (MFs), mf[q,T,n] designed for each specific sensor code. The expected temperature, T, that produces the largest correlation peak is then declared to be the actual temperature at the sensor.

Although the invention has been shown and described with respect to a certain preferred embodiment or embodiments, equivalent alterations and modifications may occur to others skilled in the art upon the reading and understanding of this specification and the annexed drawings. In particular regard to the various functions performed by the above described components (assemblies, devices, circuits, etc.), the terms used to describe such components are intended to correspond, unless otherwise indicated, to any component that performs the specified function of the described component (i.e., that is functionally equivalent), even though not structurally equivalent to the disclosed structure that performs the function in the illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

Abbreviations and acronyms used herein
ACF Autocorrelation Function
ATmp Apparent Temperature
AWSS Advanced Wireless Sensor System
IDT Inter-Digital Transducer
MF Matched Filter
PWSS Passive-Wireless SAW Strain
RA Reflector Array
RF Radio Frequency
SAW Surface Acoustic Wave

What is claimed is:

1. A surface acoustic wave sensor system for determining environmental conditions on a substrate, the system comprising:
an interrogator for producing an RF interrogating signal;
an antenna for transmitting the RF interrogating signal;
an interdigital transducer mounted on the substrate for producing an incident surface acoustic wave responsive to the RF interrogating signal;
a plurality of three or more reflector arrays mounted on the substrate for producing a like plurality of reflected surface acoustic waves responsive to the incident surface acoustic wave, a spacing between adjacent ones of the plurality of reflector arrays comprising a non-uniform distance, the plurality of reflected surface acoustic waves responsive to the environmental condition and exhibiting a characteristic from which the environmental condition can be determined; and
a processing component responsive to the plurality of reflected waves for determining the characteristic and the environmental condition;
wherein the plurality of reflector arrays comprising a first set of reflector arrays spaced according to a first minimum redundancy code and a second set of reflector arrays spaced according to a second minimum redundancy code and interleaved with the first set, the second minimum redundancy code a reverse of the first minimum redundancy code.

2. The surface acoustic wave sensor system of claim 1 wherein the characteristic comprises at least one of a differential phase shift or a differential time delay between adjacent ones of the plurality of reflected surface acoustic waves.

3. The surface acoustic wave sensor system of claim 2 wherein the processing component determines a wave velocity $V_P$ from differential phase shifts or from the time delay.

4. The surface acoustic wave sensor system of claim 1 wherein a distance from a first reflector array of the plurality of reflector arrays to a last reflector array of the plurality of reflector arrays comprises a maximum correlation distance, and wherein a sensitivity of the surface acoustic wave sensor is responsive to the maximum correlation distance.

5. The surface acoustic wave sensor system of claim 4 wherein the maximum correlation distance is populated by M reflector arrays spaced according to a minimum redundancy sequence and a unit-lag distance.

6. The surface acoustic wave sensor system of claim 1 wherein the non-uniform distance is determined according to a minimum redundancy sequence.

7. The surface acoustic wave sensor system of claim 6 wherein the minimum redundancy sequence comprises a first pair of reflector arrays spaced apart by a unit-lag distance, a second pair of reflector arrays spaced apart by a first multiple of the unit-lag distance and a third pair of reflector arrays spaced apart by a second multiple of the unit-lag distance.

8. The surface acoustic wave sensor system of claim 7 wherein a distance from a first reflector array of the plurality of reflector arrays to a last reflector array of the plurality of reflector arrays comprises a maximum correlation distance equal to a product of N and the unit-lag distance, wherein N is selected responsive to a sensitivity of the processing component.

9. The surface acoustic wave sensor system of claim 1 wherein the antenna comprises any one of a monopole antenna, a dipole antenna, and a patch antenna.

10. The surface acoustic wave sensor system of claim 1 wherein the plurality of reflector arrays comprises at least three reflector arrays.

11. The surface acoustic wave sensor system of claim 1 wherein the plurality of reflector arrays comprising a first plurality of reflector arrays in a first direction from the interdigital transducer and a second plurality of reflector arrays in a second direction from the interdigital transducer, the first direction opposite from the second direction, the interdigital transducer for producing a first incident surface acoustic wave directed toward the first plurality of reflector arrays and a second incident surface acoustic wave directed toward the second plurality of reflector arrays.

12. The surface acoustic wave sensor system of claim 1 wherein a material of the substrate comprising lithium niobate.

13. The surface acoustic wave sensor system of claim 1 wherein the environmental condition comprising one or both of temperature and strain of the substrate.

14. The surface acoustic wave sensor system of claim 1 wherein a distance between adjacent reflectors of the plurality of reflector arrays are separated by a unit lag distance that provides less than $2\pi$ radians of differential phase shift over expected environmental conditions to which the substrate is exposed.

15. The surface acoustic wave sensor system of claim 1 wherein a maximum correlation distance is selected responsive to a desired sensitivity of the sensor to changes in the environmental condition.

16. The surface acoustic wave sensor system of claim 1 wherein a desired resolution of a measure of the environmental condition is responsive to a maximum correlation distance.

17. The surface acoustic wave sensor system of claim 1 wherein the processing component uses a thermal coefficient of delay parameter in determining the characteristic and the environmental condition.

18. The surface acoustic wave sensor system of claim 1 wherein candidate impulse responses each representing a different value of the environmental condition are stored in the processing component, wherein the processing component compares an impulse response from the plurality of reflector arrays with the candidate impulse response to determine the environmental condition.

* * * * *